United States Patent
Sgroi, Jr.

(10) Patent No.: US 10,905,416 B2
(45) Date of Patent: Feb. 2, 2021

(54) OVER-MOLDED CONNECTOR FOR SURGICAL INSTRUMENTS

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 137 days.

(21) Appl. No.: 16/360,684

(22) Filed: Mar. 21, 2019

(65) Prior Publication Data

US 2019/0321033 A1 Oct. 24, 2019

Related U.S. Application Data

(60) Provisional application No. 62/661,247, filed on Apr. 23, 2018.

(51) Int. Cl.
*A61B 17/068* (2006.01)
*A61B 17/115* (2006.01)
*A61B 17/00* (2006.01)

(52) U.S. Cl.
CPC ........ *A61B 17/068* (2013.01); *A61B 17/1155* (2013.01); *A61B 2017/0023* (2013.01);
(Continued)

(58) Field of Classification Search
CPC ............................................. A61B 2017/00486
(Continued)

(56) References Cited

U.S. PATENT DOCUMENTS

| 4,731,058 A | 3/1988 | Doan |
| 4,898,360 A | 2/1990 | VonHayn et al. |

(Continued)

FOREIGN PATENT DOCUMENTS

| EP | 2316345 A1 | 5/2011 |
| EP | 2823774 A2 | 1/2015 |
| WO | 2013051076 A1 | 4/2013 |

OTHER PUBLICATIONS

Maxim Integrated Brochure (Abridged Data Sheet)—DeepCover Secure Authenticator with 1-Wire SHA-256 and 512-Bit User EEPROM, pp. 1-4 and p. 42, 2012.
(Continued)

*Primary Examiner* — Michelle Lopez
(74) *Attorney, Agent, or Firm* — Carter, DeLuca & Farrell, LLP

(57) ABSTRACT

A plug assembly for a surgical device having a loading unit includes a tray member, first and second contact members received within and extending distally from the tray member, first and second elongated electrical conductors in electrical connection with the first and second contact members and extending proximally from the tray member, an outer case formed about the tray member and the proximal portion of the first and second contact members, and a seal member received about the first and second contact members adjacent the outer tray. Each of the first and second contact members includes proximal and distal portions and an extension formed on the proximal portions. Each of the first and second elongated electrical conductors includes proximal and distal portions and a loop formed on the distal portion. The loop of each of the first and second elongated electrical conductors is received about the extension of the respective first and second contact members.

20 Claims, 12 Drawing Sheets

(52) U.S. Cl.
CPC ............... *A61B 2017/00398* (2013.01); *A61B 2017/00473* (2013.01); *A61B 2017/00486* (2013.01)

(58) Field of Classification Search
USPC ...................................................... 227/175.1
See application file for complete search history.

(56) References Cited

U.S. PATENT DOCUMENTS

| | | | |
|---|---|---|---|
| 5,391,166 | A | 2/1995 | Eggers |
| 5,954,535 | A | 9/1999 | Lawrence |
| 5,971,801 | A | 10/1999 | Kato et al. |
| 6,727,477 | B1 | 4/2004 | Li-Chen |
| 6,988,897 | B2 | 1/2006 | Belongia et al. |
| 7,721,931 | B2 | 5/2010 | Shelton, IV et al. |
| 7,887,530 | B2 | 2/2011 | Zemlok et al. |
| 8,397,971 | B2 | 3/2013 | Yates et al. |
| 8,628,467 | B2 | 1/2014 | Whitman et al. |
| 8,862,209 | B2 | 10/2014 | Whitman et al. |
| 9,022,274 | B2 | 5/2015 | Penna |
| 9,351,724 | B2 | 5/2016 | Penna |
| 9,636,112 | B2 * | 5/2017 | Penna .................... H05K 5/069 |
| 9,833,235 | B2 * | 12/2017 | Penna .................. H05K 7/1427 |
| 2001/0031975 | A1 | 10/2001 | Whitman et al. |
| 2005/0272565 | A1 | 12/2005 | Hao |
| 2007/0023477 | A1 | 2/2007 | Whitman et al. |
| 2008/0242510 | A1 | 10/2008 | Topel et al. |
| 2009/0054208 | A1 | 2/2009 | Wu |
| 2009/0057369 | A1 | 3/2009 | Smith et al. |
| 2009/0090763 | A1 | 4/2009 | Zemlok et al. |
| 2011/0022032 | A1 | 1/2011 | Zemlok et al. |
| 2011/0125138 | A1 | 5/2011 | Malinouskas et al. |
| 2011/0155784 | A1 | 6/2011 | Shelton, IV et al. |
| 2011/0192884 | A1 | 8/2011 | Whitman et al. |
| 2012/0061447 | A1 | 3/2012 | Williams et al. |
| 2012/0071866 | A1 | 3/2012 | Kerr et al. |
| 2012/0089131 | A1 | 4/2012 | Zemlok et al. |
| 2012/0116388 | A1 | 5/2012 | Houser et al. |
| 2012/0209288 | A1 | 8/2012 | Robinson |
| 2013/0098966 | A1 | 4/2013 | Kostrzewski et al. |
| 2013/0123822 | A1 | 5/2013 | Wellman et al. |
| 2013/0131650 | A1 | 5/2013 | Whitman et al. |
| 2013/0324979 | A1 | 12/2013 | Nicholas et al. |
| 2015/0014393 | A1 | 1/2015 | Milliman |
| 2015/0048140 | A1 | 2/2015 | Penna et al. |
| 2015/0053749 | A1 | 2/2015 | Shelton, IV et al. |
| 2015/0216525 | A1 | 8/2015 | Collins et al. |
| 2016/0106406 | A1 | 4/2016 | Cabrera et al. |
| 2016/0265938 | A1 * | 9/2016 | Hryb .................. A61B 17/1155 |

OTHER PUBLICATIONS

"IC-On-Line" DS28E15-1-Wire SHA-256 Secure Authenticator with 512-Bit User EEPROM, located at: <http://www.ic-on-line.cn/view.sub.--download>.

European Search Report dated Aug. 27, 2019, issued in EP Appln. No. 19170305.

* cited by examiner

OVER-MOLDED CONNECTOR FOR SURGICAL INSTRUMENTS

CROSS-REFERENCE TO RELATED APPLICATIONS

This application claims the benefit of and priority to U.S. Provisional Patent Application Ser. No. 62/661,247 filed Apr. 23, 2018, the entire disclosure of which is incorporated by reference herein.

BACKGROUND

Technical Field

This disclosure relates to reusable powered surgical instruments. More specifically, this disclosure relates to electronic connectors for use in reusable powered staplers.

Background of Related Art

Powered surgical instruments for use in endoscopic procedures are known. Typically, such instruments include a reusable handle assembly and a disposable end effector. An adapter assembly may connect the end effector to the reusable handle assembly. In the case of a surgical stapler, the end effector includes a disposable cartridge or reload assembly that is changed after each firing of the surgical stapler. To reduce costs and shorten procedure times, the reusable handle assemblies are generally configured for use with a variety of reload assemblies of various configurations for use on tissue having different properties, e.g., thickness, density. For example, the different reload assemblies may have staples of different sizes and/or the staples may be arranged in different configurations.

To ensure the reusable handle assembly is programmed to operate with the attached reload assembly, some reload assemblies are provided with a chip that communicates to the reusable handle assembly the configuration of the reload assembly. As such, the configuration of the reload assembly is automatically relayed to the reusable handle assembly upon attachment of the reload assembly to the reusable handle assembly, thereby eliminating any user error that may be experienced during manual programming of the reusable handle assembly when switching between reload assemblies with different configurations. The reload assemblies and reusable handle assemblies may also be configured to prevent firing of a reload assembly that has already been used.

Surgical staplers are generally used for stapling tissue within a body cavity where the surgical staplers are likely to come in contact with fluids, e.g., blood, bile, irrigation solutions. Following the surgical procedure, the reload assemblies are disposed of in a traditional manner, and the reusable handle assemblies are cleaned and sterilized. The cleaning and sterilizing processes may include the use of a high PH solution, e.g, potassium hydroxide, which can be harsh on sensitive electronic components. Sterilization is typically performed using an autoclave process in which the device is subjected to high temperature and high pressure steam, both of which are detrimental to the electronic components.

Therefore, it would be beneficial to have a reusable unit that can withstand the harsh environments of common disinfecting and/or sterilization processes.

SUMMARY

A surgical stapling device is disclosed. The surgical stapling device includes a handle assembly, an adapter assembly extending from the handle assembly and including a distal portion configured for operable engagement with a loading unit, and a plug assembly disposed within the distal portion of the adapter assembly and configured for electrical connection with a chip assembly in a loading unit. The plug assembly includes a tray member, first and second contact members received within and extending distally from the tray member, first and second elongated electrical conductors in electrical connection with the first and second contact members and extending proximally from the tray member, an outer case formed about the tray member and the proximal portion of the first and second contact members, and a seal member received about the first and second contact members adjacent the outer tray. Each of the first and second contact members includes proximal and distal portions and an extension formed on the proximal portions. Each of the first and second elongated electrical conductors includes proximal and distal portions and a loop formed on the distal portion. The loop of each of the first and second elongated electrical conductors is received about the extension of the respective first and second contact members.

In embodiments, the outer case of the plug assembly is overmolded about the tray member and the proximal portion of the first and second contact members. The surgical stapling device may include a loading unit. The loading unit may include a chip assembly configured for electrical connection with the plug assembly.

The plug assembly may further include a block member received between the first and second contact members. The tray member may define first and second channels, and the first and second contact members are received within the respective first and second channels. The first and second elongated electrical conductors may be received within the respective first and second channels. The first and second contact members and the first and second elongated electrical conductors may be secured within the respective first and second channels with a sealant material. In embodiments, the sealant material is an epoxy.

The outer case may include a cylindrical projection configured to facilitate connection of the plug assembly with the adapter assembly. The first and second elongated electrical conductors are electrically connected to the handle assembly. The outer case may include a distally extending extension and the seal member may be secured to the extension.

Also disclosed is a plug assembly for a surgical device having a loading unit. The plug assembly includes a tray member, first and second contact members received within and extending distally from the tray member, first and second elongated electrical conductors in electrical connection with the first and second contact members and extending proximally from the tray member, an outer case formed about the tray member and the proximal portion of the first and second contact members, and a seal member received about the first and second contact members adjacent the outer tray. Each of the first and second contact members includes proximal and distal portions and an extension formed on the proximal portions. Each of the first and second elongated electrical conductors includes proximal and distal portions and a loop formed on the distal portion. The loop of each of the first and second elongated electrical conductors is received about the extension of the respective first and second contact members.

BRIEF DESCRIPTION OF THE DISCLOSURE

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION OF THE EMBODIMENTS

Figure 1:
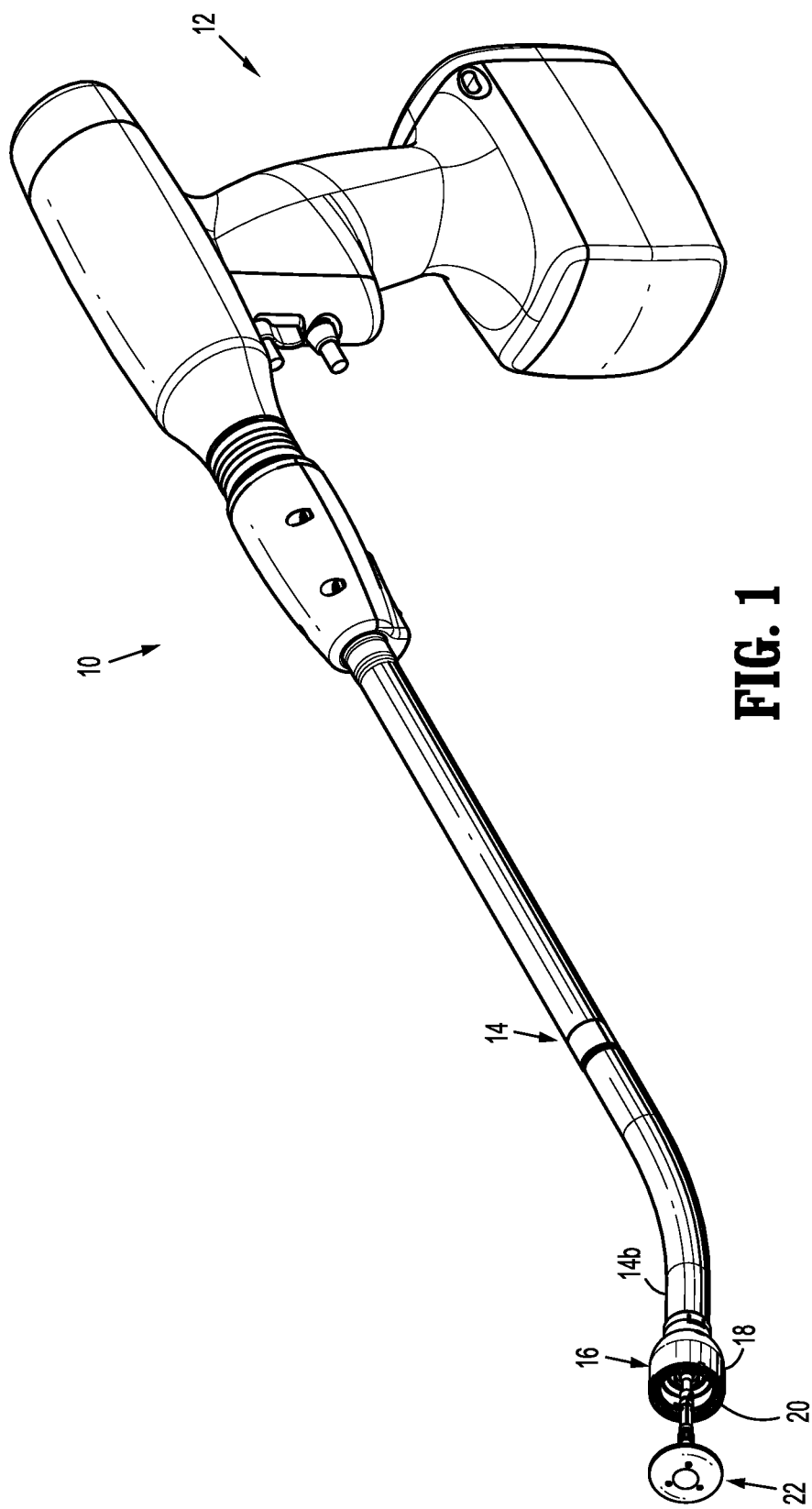
FIG. 1 is a perspective view of a surgical stapling device suitable for use with the plug assemblies of the present disclosure.

Embodiments of the presently disclosed plug assemblies will now be described in detail with reference to the drawings in which like reference numerals designate identical or corresponding elements in each of the several views. As is common in the art, the term "proximal" refers to that part or component closer to the user or operator, e.g. surgeon or clinician, while the term "distal" refers to that part or component further away from the user.

Although the plug assemblies of the present disclosure will be shown and described as relates to circular stapling devices, the aspects of the present disclosure may be modified for use with any reusable surgical device utilizing a disposable and/or separable loading unit.

With reference initially to FIG. 1, a surgical stapling instrument suitable for use with a plug assembly of the present disclosure is shown generally as circular stapler 10. The circular stapler 10 includes a handle assembly 12 and an adapter assembly 14 removably attached to, and extending distally from handle assembly 12. A detailed description of an exemplary handle assembly is disclosed in commonly owned U.S. Pat. App. Pub. No. 2012/0089131 ("the '131 publication"), and a detailed description of an exemplary adapter assembly is disclosed in commonly owned U.S. Pat. App. Pub. No. 2016/0106406 ("the '406 publication"). The content of each of the '131 and '406 publications is incorporated herein by reference in their entirety.

Figure 2:
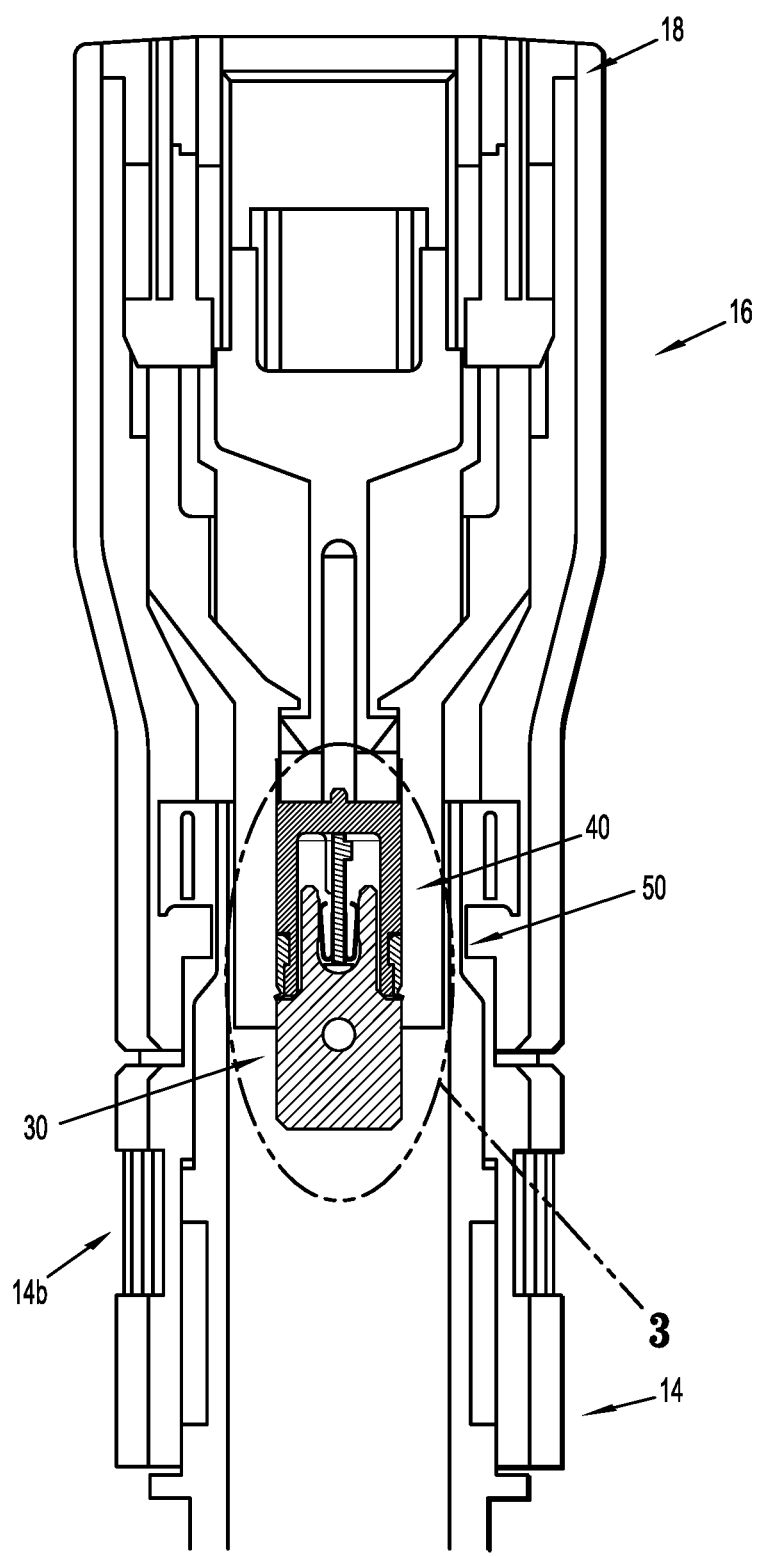
FIG. 2 is a cross-sectional view of a loading unit and a distal portion of an adapter assembly of the surgical stapling device shown in FIG. 1, including a connector assembly having a plug assembly and a chip assembly.

With additional reference to FIG. 2, a reload assembly 16 is selectively secured to a distal portion 14b of adapter portion 14. Briefly, the reload assembly 16 includes a cartridge assembly 18 supporting a plurality of staples (not shown). A trocar 20 extends through the reload assembly 16 and is configured for releasable connection with an anvil assembly 22. For a detailed description of exemplary reload assemblies, please refer to commonly owned. U.S. Pat. No. 9,351,724 ("the '724 patent") and U.S. Pat. No. 9,022,274 ("the '274 patent"), the disclosures of which are incorporated herein by reference their entirety.

Figure 3:
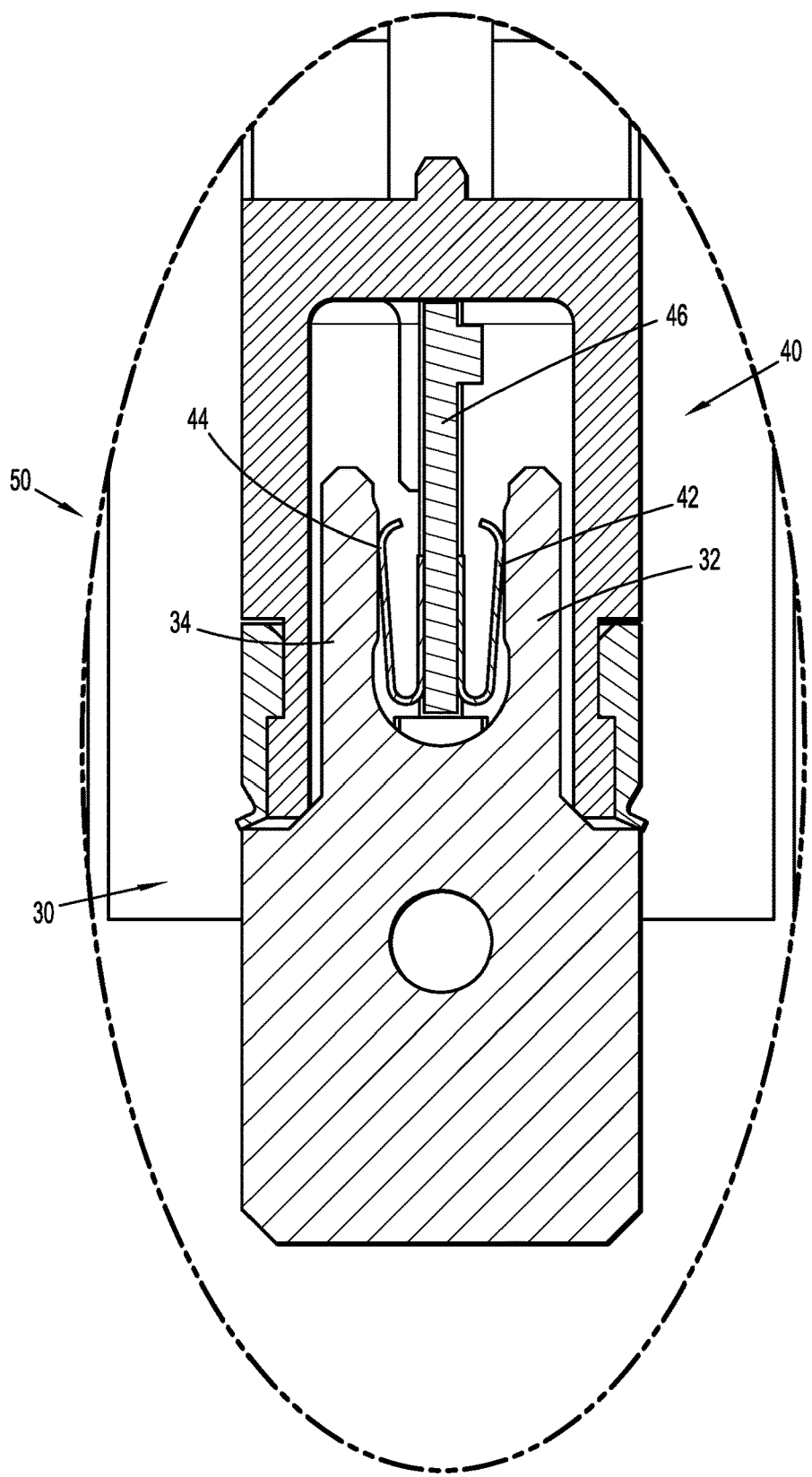
FIG. 3 is an enlarged view of the indicated area of detail shown in FIG. 2.
Figure 4:
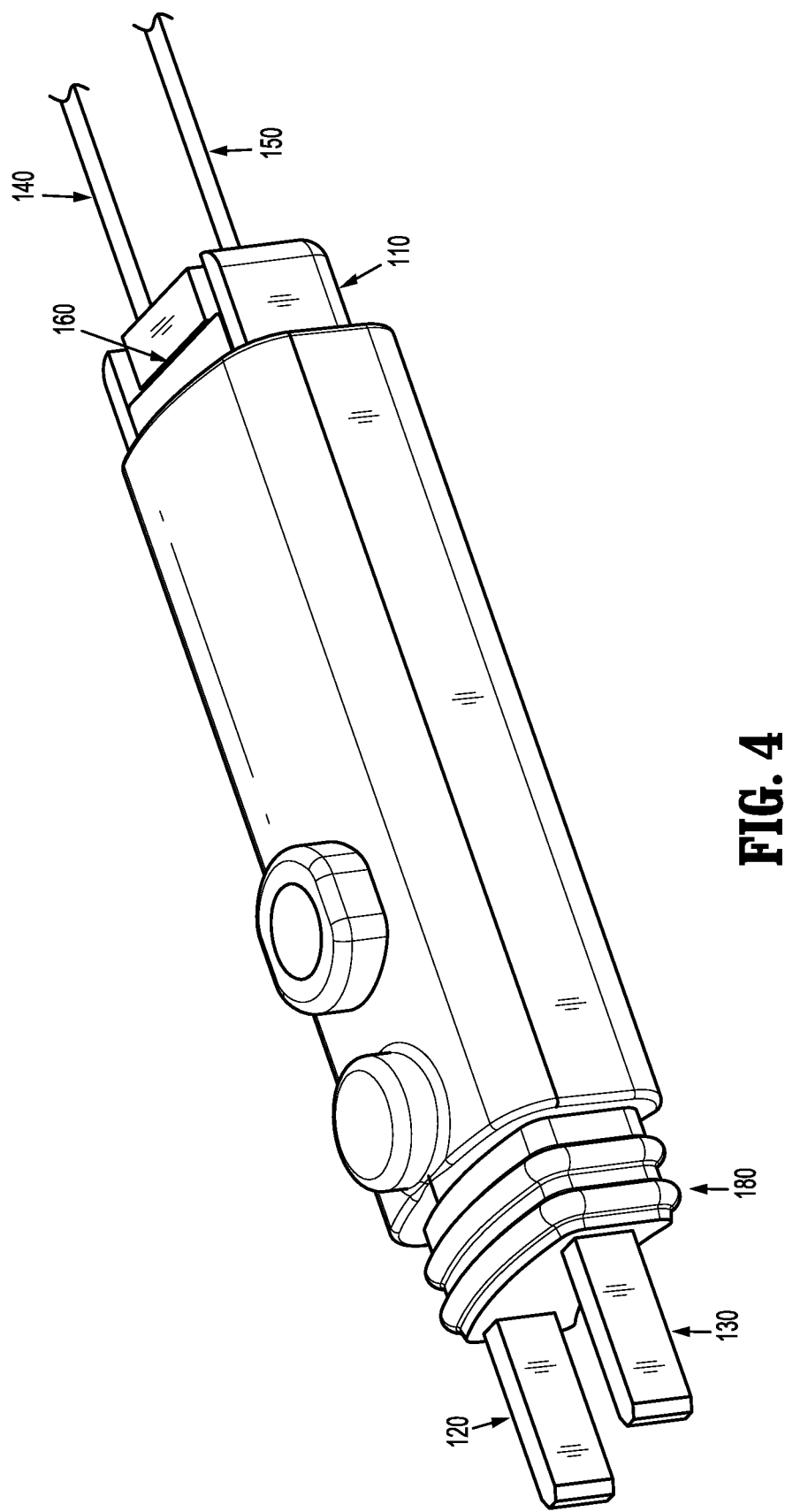
FIG. 4 is a perspective view of a plug assembly according to an embodiment of the present disclosure.

With reference now to FIGS. 2 and 3, disposed within the distal portion 14b of the adapter portion 14 of the circular stapler 10 (FIG. 1) is a plug assembly 30. The plug assembly 30 is configured to electrically couple with a chip assembly 40 disposed within the reload assembly 16. The plug and chip assemblies 30, 40 (collectively, connector assembly 50) are configured such that when the reload assembly 16 is secured to the adapter portion 14 of the circular stapler 10, connector members 32, 34 of the plug assembly 20 engage contact members 42, 44, respectively, of the chip assembly 40. Engagement between the connector members 32, 34 and the contact members 42, 44, respectively, electrically couple a chip 46 disposed within the chip assembly 40 with a control unit (not shown) disposed within the handle assembly 12. For a detailed description of an exemplary connector assembly please refer to commonly owned U.S. Pat. No. 9,833,235, the content of which is incorporated herein by reference in its entirety.

The harsh environments of disinfecting and sterilization require components that can withstand such methods. These components include pc boards, electronic components such as resistors, diodes, microprocessors, and the like. In many instances, it is necessary to also have connectors that can withstand the harsh environments of common disinfecting and sterilization process such as, for example, high PH auto washers and steam autoclaves.

With reference now to FIGS. 4-10 a plug assembly according to a first embodiment of the present disclosure is shown as plug assembly 100. The plug assembly 100 includes a tray member 110, first and second contact members 120, 130 supported within and extending distally from the tray member 110, first and second elongated electrical conductors 140, 150 connected to and extending proximally from the respective first and second contact members 120, 130, respectively, a base or block member 160 received between the first and second contact members 120, 130, an outer case 170 received about the tray member 110, and a seal member 180 received about the first and second contact members 120, 130 and over a distal extension 172 of the outer case 170.

Figure 5:
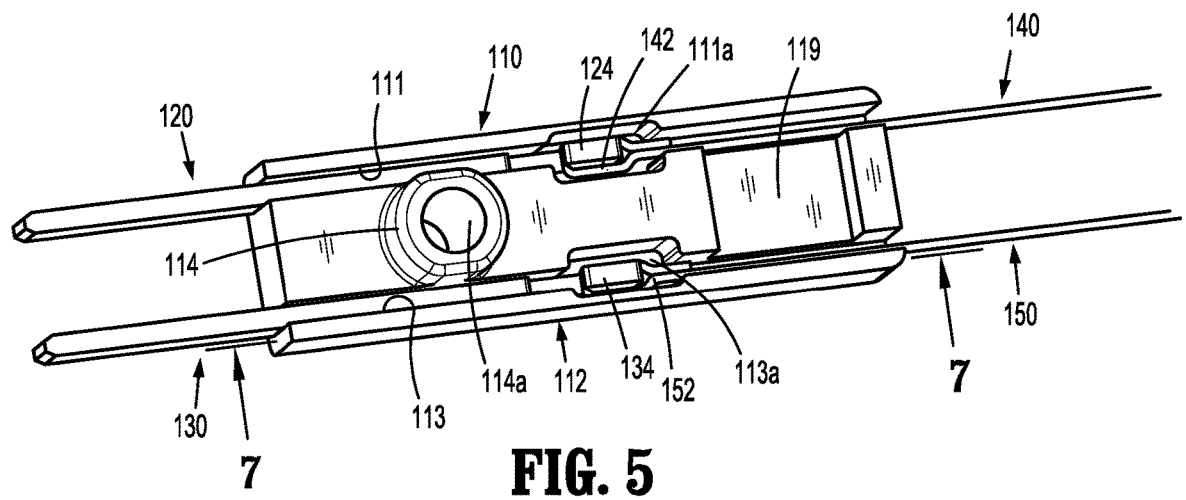
FIG. 5 is a perspective top view of a tray member, contact members and elongated electrical conductors of the plug assembly shown in FIG. 4.

With particular reference to FIG. 5, the tray member 110 of the plug assembly 100 includes a substantially rectangular body 112 and is formed from a material that can withstand common disinfecting and sterilization processes. In embodiments, tray member 110 is molded using Sabic Noryl HNA055-111S resin.

The tray member 110 of the plug assembly 100 is configured to support the first and second contact members 120, 130. More particularly, the tray member 110 defines first and second channels 111, 113 extending a length of the rectangular body 112 for receiving the respective first and second contact members 120, 130. The rectangular body 112 further defines first and second reliefs 111a, 113a along the respective first and second channels 111, 113, first and second cutouts 115, 117 (FIG. 7; only one shown) along each of the first and second channels 111, 113, and a recess 119 disposed between the first and second channels 111, 113. The first and second reliefs 111a, 113a are configured to accommodate the connection between the respective first and second contact members 120, 130 and the respective elongated electrical conductors 140, 150. The first and second cutouts 115, 117 along each of the first and second channels 111, 113 are configured to longitudinally secure each of the respective first and second contact members 120, 130 within the tray member 110. The recess 119 is configured to receive the block member 160.

The tray member 110 of the plug assembly 100 includes an annular flange 114 extending outwardly from the rectangular body 112 defining a throughbore 114a. The annular flange 114 is configured to facilitate attachment of the plug assembly 100 within and to the adapter assembly 14 (FIG. 2).

Figure 6:
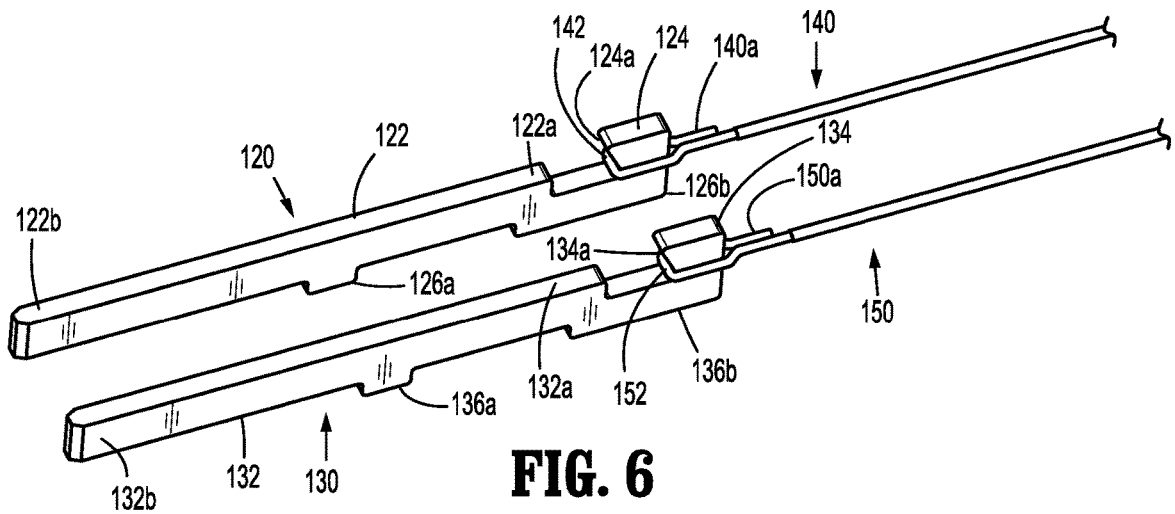
FIG. 6 is a perspective view of the contact members and elongated electrical conductors of the plug assembly shown in FIG. 4.

Turning now to FIG. 6, each of the first and second contact members 120, 130 includes an elongate body 122, 132, respectively, having proximal and distal portions 122a, 132a, 122b, 132b. The first and second contact members 120, 130 may be formed from metal, alloy, or any other suitable material. In embodiments, the first and second contact members 120, 130 are formed from 301 SS (UNS 530100) ½ HARD and are under-plated using 50 microinches of electroless nickel plating Type V and 30 microinches of gold plating type III. This two-step plating process facilitates the soldering process and allows for optimum adhesion.

The proximal portions 122a, 132a of the respective first and second contact members 120, 130 are configured for operable engagement with the respective first and second elongated electrical conductors 140, 150. More particularly, each of the first and second proximal portions 122a, 132.a includes an extension 124, 134. The extensions 124, 134 each include an angled distal facing surface 124a, 134b about which a loop 142, 152, respectively, of the respective first and second elongated electrical conductors 140, 150 is received. The extensions 124, 134 provide a hook-type mechanical connection for connecting the first and second contact members with the respective first and second elongated electrical conductors 140, 150. The distal portions 122b, 132b of the respective first and second contact members 120, 130 are configured for operable engagement with first and second contact members 42, 44 (FIG. 3), respectively, of the chip assembly 40.

Figure 7:
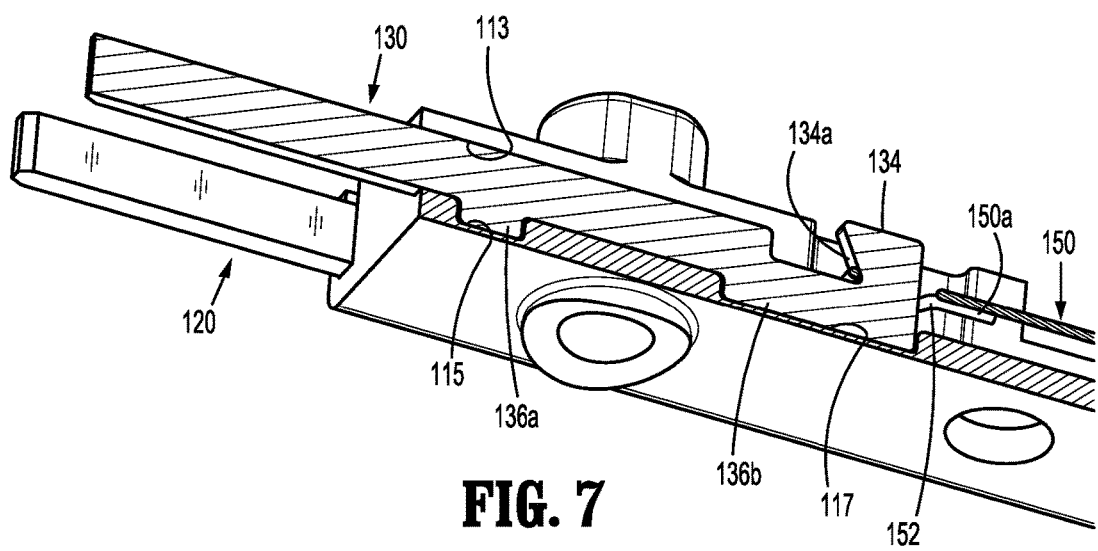
FIG. 7 is a perspective cross-sectional view taken along line 7-7 shown in FIG. 5.

Still referring to FIG. 6, each of the first and second contact members 120, 130 of the plug assembly 100 include a first tab 126a, 136a, respectively, and a second tab 126b, 136b, respectively. The first tabs 126a, 136a of the respective first and second contact members 120, 130 are receivable within the first cutouts 115 (FIG. 7; only one shown) in the tray member 110 (FIG. 7) and the second tabs 126b, 136b of the respective first and second contact members 120, 130 are receivable within the second cutouts 117 (FIG. 7; only one shown) in the tray member 110 (FIG. 7). The first and second tabs 126a, 126b, 136a, 136b of the respective first and second contact members 120, 130 prevent longitudinal movement of the first and second contact members 120, 130 relative to the tray member 110.

Although the first and second elongated electrical conductors 140, 150 are shown and described as first and second wires, it is envisioned that the elongated electrical conductors 140, 150 may also include flex cables or other suitable conductors. In embodiments, the first and second elongated electrical conductors 140, 150 include Peek insulated wires having 0.005" wall thickness of Peek.

With continued reference to FIG. 6, a distal portion 140a, 150a of each of the first and second elongated electrical conductors 140, 150 are folded on each other to form a loop 142, 152, respectively. The loop 142, 152 of each of the respective first and second elongated electrical conductors 140, 150 may be maintained by wrapping the distal portion 140a, 150a of the respective first and second elongated electrical conductors 140, 150 about the first and second elongated electrical conductors 140, 150, respectively. Alternatively, the distal ends 140a, 150a may be secured to the respective first and second elongated electrical conductors 140, 150 using welding, soldering, adhesive, or in any suitable manner. In embodiments, the loops 142, 152 are maintained in the respective first and second elongated electrical conductors 140, 150 as formed because of the stiffness of the material from which the first and second elongated electrical conductors 140, 150 are formed. The loops 142, 152 on each of the first and second elongated electrical conductors 140, 150, respectively, provide pull-out resistance to the respective first and second elongated electrical conductors 140, 150 to prevent the first and second elongated electrical conductors 140, 150 from becoming detached from the first and second contact members 120, 130, respectively.

During manufacture of the plug assembly 100, the loops 142, 152 of the respective first and second elongated electrical conductors 140, 150 are received over the respective extensions 124, 134 of the first and second contact members 120, 130. The inclined surface 124a, 134a of the extensions 124, 134, respectively, facilitate engagement of the respective loops 142, 152 with the respective first and second contact members 140, 150.

Once the loops 142, 152 of the respective first and second elongated electrical conductors 140, 150 are secured to the first and second contact members 120, 130, respectively, the first and second contact members 120, 130 are received within the first and second channels 111, 113, respectively, of the tray member 110. The extension 124, 134 of each of the first and second contact members 120, 130, with the respective loops 142, 152 attached, is received within the respective first and second reliefs 111a, 113a formed along the respective first and second channels 111, 113 in the tray member 110.

The configuration of the first and second reliefs 111a, 113a may assist in maintaining the loops 142, 152 in each of the respective first and second elongated electrical conductors 140, 150. More particularly, the width of each of the first and second reliefs 111a, 113a may be such that the loops 142, 152 are prevented from unwrapping from about the extensions 124, 134, respectively. In this manner, the loops 142, 152 of the first and second elongated electrical conductors 140, 150, respectively, are prevented from pulling-out or becoming disconnected from the respective first and second elongated electrical conductors 140, 150.

When the first and second contact members 120, 130 of the plug assembly 100 are received within the respective first and second channels 111, 113 of the tray member 110, the first tabs 126a, 136a of the respective first and second contact members 120, 130 are received within the first cutouts 115 (FIG. 7; only one shown) in the tray member 110 and the second tabs 126b, 136b of the respective first and second contact members 120, 130 are received within the second cutouts 117 (FIG. 7; only one shown) in the tray member 110. As noted above, the receipt of the first and second tabs 126a, 136a, 126b, 136b of the respective first and second contact members 120, 130 within the respective first and second cutouts 115, 117 of the first and second channels 111, 113 longitudinally fix the first and second contact members 120, 130 relative to the tray member 110.

Figure 8:
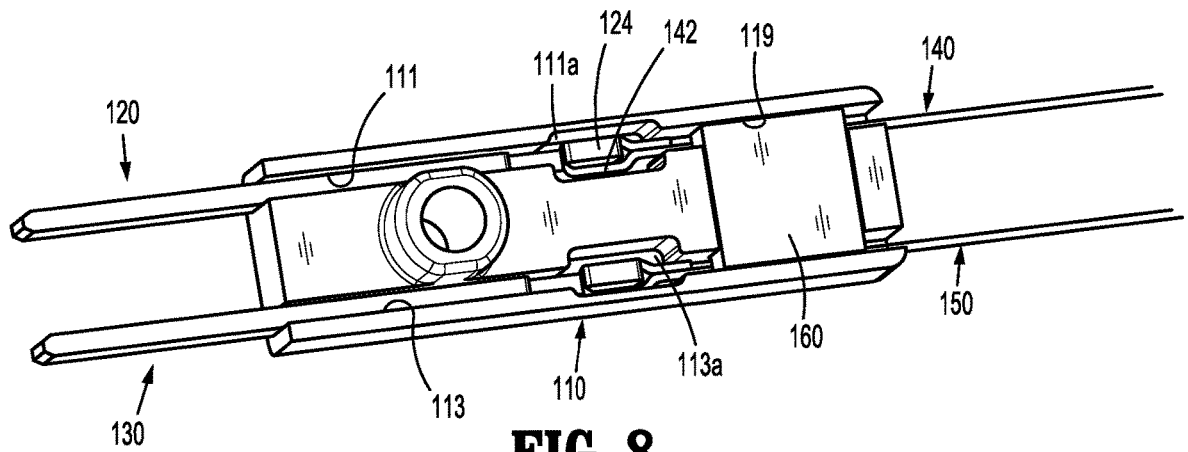
FIG. 8 is a perspective top view of the tray member, contact member, and elongated electrical conductors shown in FIG. 4, and further including a block member.

Turning to FIG. 8, after receiving the first and second contact members 120, 130 within the respective first and second channels 111, 113 in the tray member 110, the block member 160 is received within recess 119 of the tray member 110 to further secure the first and second elongated electrical conductors 140, 150 and the respective first and second contact members 120, 130 together and within the tray member 110. The recess 119 may be configured such that an interference fit is created between the block member 160 and the tray member 110. In embodiments, the interference is from 0.005 to 0.0015 inches. Alternatively, the block member 160 may fit within the recess 119 with a clearance fit. The depth of the recess 119 is such that when the block member 160 is received within the recess 119, a top surface of the block member 160 is substantially coplanar with the top surface of the tray member 110. The block member 160 is formed from a material that can withstand common disinfecting and sterilization processes. In embodiments, the block member 160 is molded using Sabic Noryl HNA055-111S resin.

Once the block member 160 is received within the recess 119 in the tray member 110, material is applied within the first and second channels 111, 113 and reliefs 111a, 113a to seal member the first and second channels 111, 113 and the reliefs 111a, 113a. The seal membering material may be a thermo-set material, and may include silicones, epoxies, polyurethanes, and the like. In embodiments, the thermo-set material is a two part POLYBUTADIENE rubber sold by Von-Roll (John C. Dolph Company). In embodiments, UV or light cured resins are utilized to better control the cure of the material. For example, the light cure or UV cure resins may include Loctite 5055, Loctite 3301, Loctite 3321, Loctite 3335, Loctite UV88001, Loctite UV3000, Loctite5055, Loctite 5140, and the like.

Figure 9:
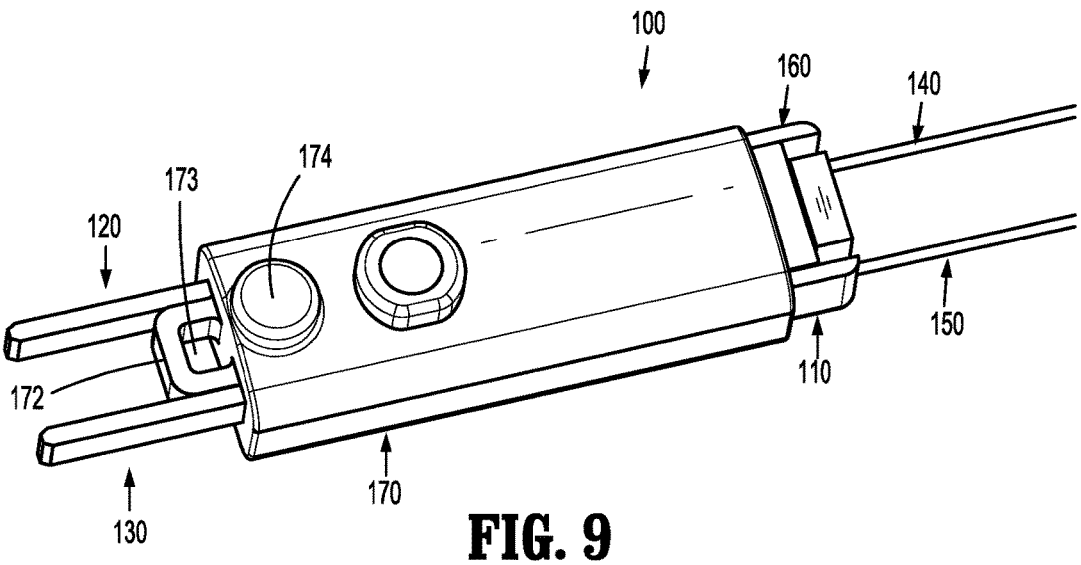
FIG. 9 is a perspective top view of plug assembly shown in FIG. 4, without a seal member.
Figure 10:
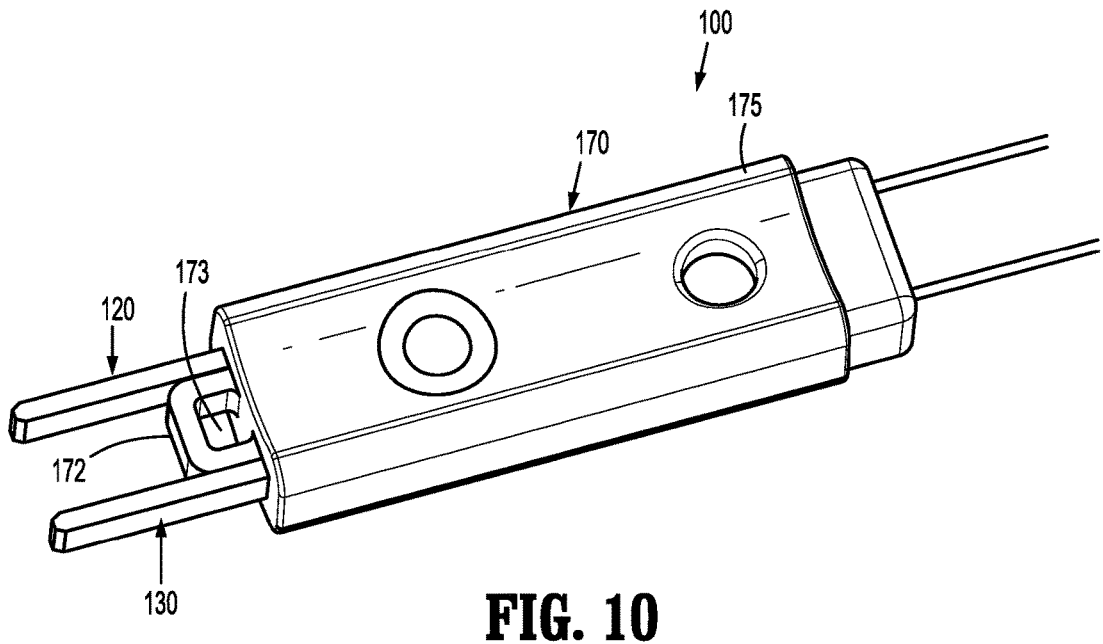
FIG. 10 is a perspective bottom view of the plug assembly shown in FIG. 9.

Turning to FIGS. 9 and 10, the outer case 170 of the plug assembly 100 is then received over the tray member 110. The outer case 170 is formed of a material that can withstand common disinfecting and sterilization processes. In embodiments, the outer case 170 is molded using Sabic Noryl HNA055-111S resin. In embodiments, the outer case 170 is formed directly about the tray member 110. For example, the outer case 170 may be molded over the tray member 110 (overmolded). The outer case 170 includes an extension 172 extending between the first and second contact members 120, 130. The extension 172 defines a slot or opening 173. The extension 172 is configured to facilitate the attachment of the seal member 180 (FIG. 4) about the first and second contact members 120, 130 and to the tray member 110. The outer case 170 further includes a cylindrical projection 174 extending outwardly and disposed adjacent the annular flange 114 of the tray member 110. On a side opposite the cylindrical projection 174, the outer case 170 defines a circular recess 175.

The seal member 180 (FIG. 4) of the plug assembly 100 is fabricated using a low durometer (e.g. rubber properties) resin that can withstand common disinfecting and sterilization processes. In embodiments, the seal member 180 is compression molded using Elastosil LR 3003/60 W AB-LSR Silicone. However, other suitable materials are possible, including injection molded resins. In embodiments, the seal member 180 is directly formed over the first and second contact members 120, 130 adjacent a distal portion of the tray member 110 using, for example, an overmolding process. Alternatively, the seal member 180 is formed as a separate component that is then received about the first and second contact members 120, 130 and the extension 172 of the tray member 170.

Figure 11:
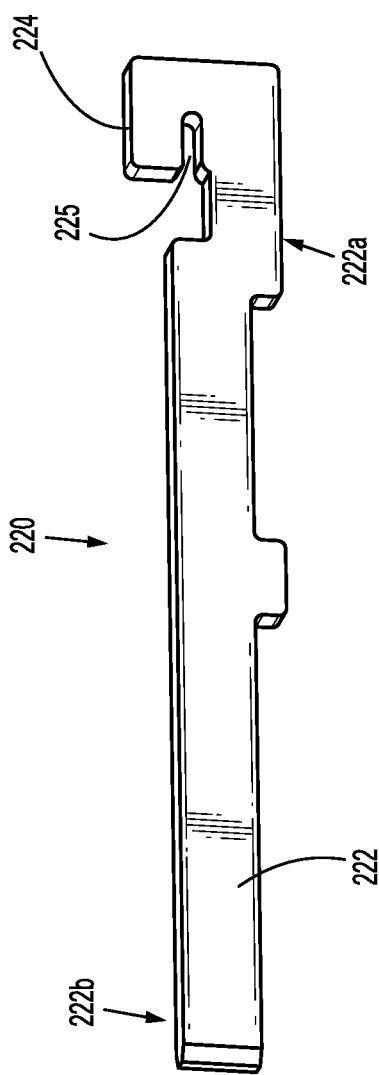
FIG. 11 is a perspective side view of a contact member according to another embodiment of the present disclosure.
Figure 12:
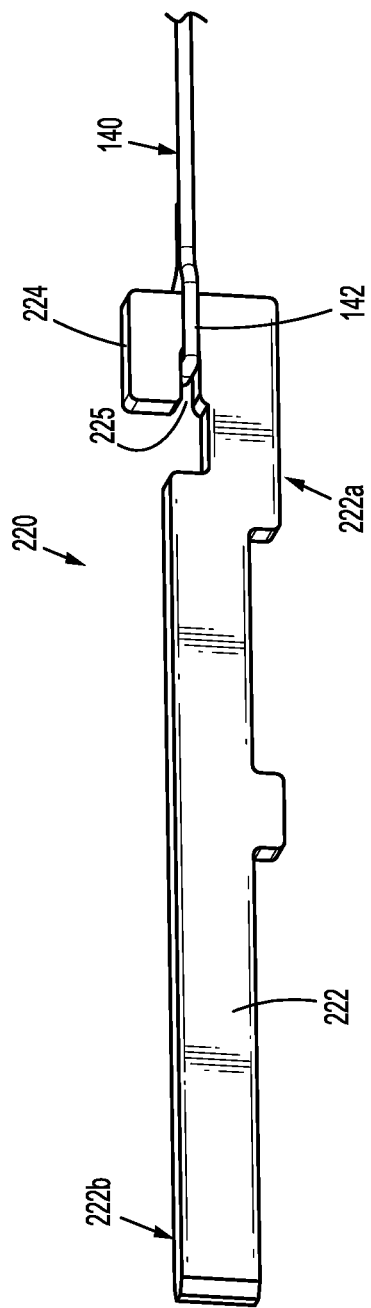
FIG. 12 is a perspective side view of the contact member shown in FIG. 11, connected to an elongated electric conductor.

With reference now to FIGS. 11 and 12, an alternative embodiment of the first and second contact members 120, 130 is shown as contact member 220. The contact member 220 is configured for electrical connection to the elongated electric conductor 140 (FIG. 12) without the need for soldering the contact member 220 and the elongated electric conductor 140 together. The contact member 220 is substantially similar to the first and second contact members 120, 130 described herein above, and will only be described in detail as relates to the difference therebetween.

With continued reference to FIGS. 11 and 12, the contact member 220 includes an elongate body 222 having proximal and distal portions 222a, 222b. The proximal portion 222a of the contact member 220 is configured for operable engagement with the elongated electric conductor 140 (FIG. 12). More particularly, the proximal portion 222a of the contact member 220 includes an extension 224. The extension 224 of the contact member 220 defines a slot 225 having a distal facing opening. The slot is configured to receive the loop 142 of the elongated electric conductor 140. In embodiments, the slot 225 is tapered in the proximal direction to facilitate a friction fit with the loop 142.

Alternatively, after the loop 142 of the elongated electric conductor 140 is received within the slot 225 formed in the extension 224 of the contact member 220, the extension 224 is bent towards the elongate body 222 of the contact member 220 to cause the narrowing of the slot 225. This narrowing of the slot 225 squeezes or crimps the loop 142 of the elongated electric conductor 140, thereby securing the loop 142 within the slot 225 and ensuring an electrical connection between the contact member 220 and the elongated electric conductor 140. The contact member 220 and the elongated electric conductor 140 may additionally be soldered together to further ensure the connection between the contact member 220 and the elongated electric conductor 140.

Figure 13:
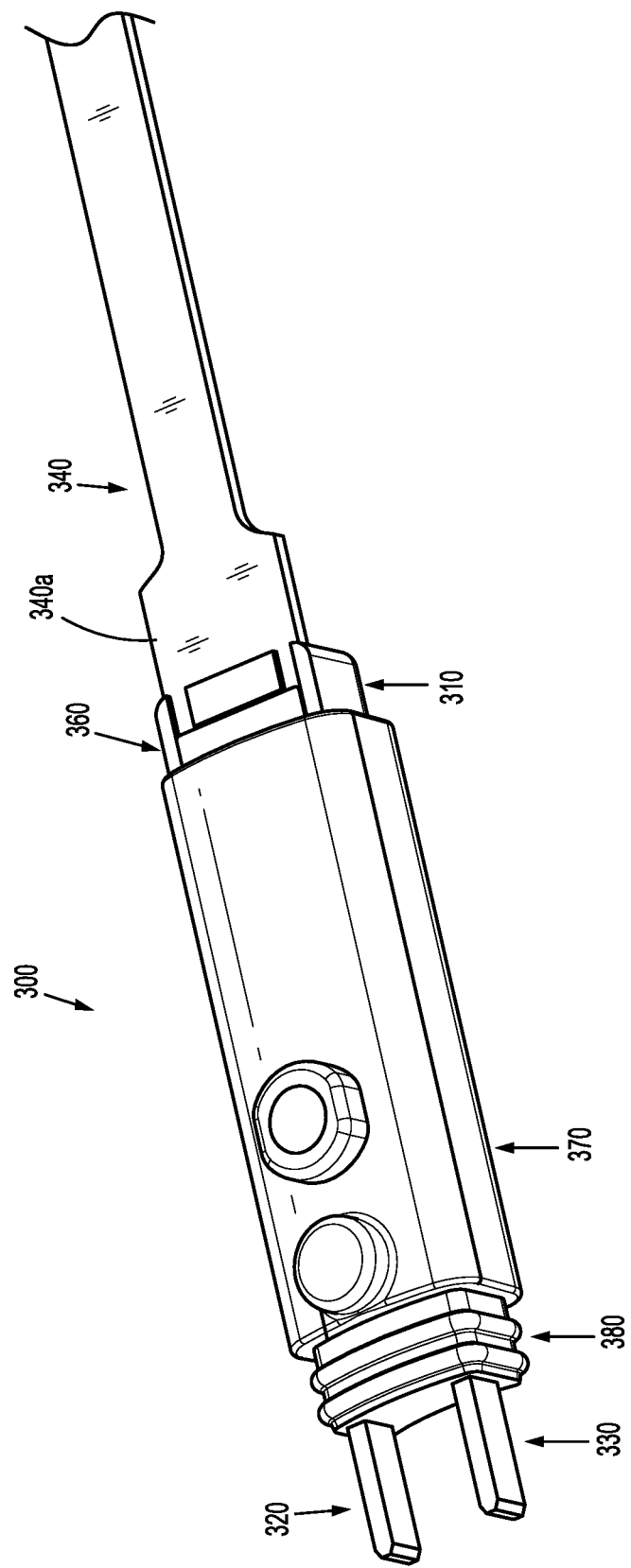
FIG. 13 is a perspective view of a plug assembly according to another embodiment of the present disclosure.
Figure 14:
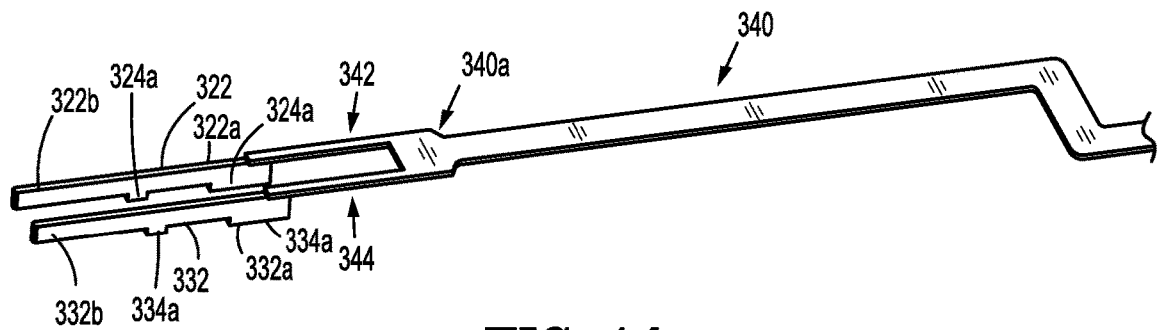
FIG. 14 is a perspective view of contact members and a flexible cable of the plug assembly shown in FIG. 13.
Figure 15:
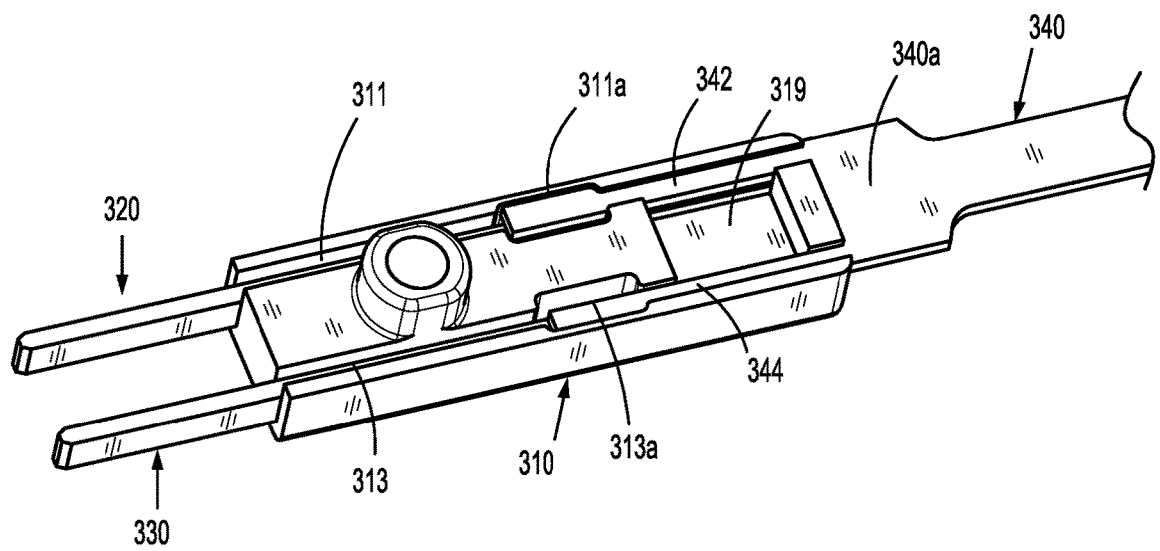
FIG. 15 is a perspective view of the contact members and flexible cable shown in FIG. 14 received within a tray member.

With reference now to FIGS. 13-15, another embodiment of a plug assembly according to the present disclosure is shown as plug assembly 300. The plug assembly 300 is substantially similar to plug assembly 100 described herein, and will only be described in detail to the extent necessary to full disclose the aspects of the present disclosure.

With particular reference to FIG. 13, the plug assembly 300 includes a tray member 310, first and second contact members 320, 330 supported within and extending distally from the tray member 310, a flexible cable 340 connected to and extending proximally from the first and second contact members 320, 330 and the tray member 310, a base or block member 360 received between the first and second contact members 320, 330, an outer case 370 received about the tray member 310, and a seal member 380 formed about the first and second contact members 320, 330 adjacent the outer case 370.

Turing to FIG. 14, each of the first and second contact members 320, 330 includes an elongate body 322, 332, respectively, having a proximal portion 322a, 332a, respectively, and a distal portion 322b, 332b, respectively. The flexible cable 340 includes a distal portion 340a having first and second extensions 342, 344. The first extension 342 of the flexible cable 340 is secured to the proximal portion 322a of the first contact member 320 and the second extension 344 of the flexible cable 340 is secured to the proximal portion 332a of the second contact member 330 in any suitable manner. In embodiments, and as shown, the first and second extensions 342, 344 are soldered to the respective first and second contact members 320, 330.

Once the flexible cable 340 is secured to the first and second contact members 330, 340, the first and second contact members 330, 340 are received within respective first and second channels 311, 313 of the tray member 310. The first and second contact members 330, 340 are prevent from longitudinal movement within the respective first and second channels 311, 313 by first and second tabs 324a, 334a, 324b, 324b. The block member 360 (FIG. 13) is received within recess 319 in the tray member 310 and is configured to secure the distal portion 340a of the flexible cable 340 within the tray member 310. An epoxy or other material may then be injected, or otherwise received, within the first and second channels 311, 313 to further secure the first and second contact members 320, 330 and the distal portion 340a of the flexible cable 340 within the tray member 310.

It is envisioned that each of the first and second extensions 342, 342 of the flexible cable 340 may include an enlarged portion (not shown) that conforms with reliefs 311a, 313a formed along respective first and second channels 311, 313 within tray member 310. The enlarged portions would assist in preventing the first and second extensions 342, 344 of the flexible cable 340 from being pulled out of the tray member 310, and thereby preventing separation from the respective first and second contact members 320, 330. By including the enlarged portions on each of the first and second extensions 342, 344 of the flexible cable 340, the first and second extensions 342, 344 of the flexible cable 340 may need not be soldered to the respective first and second contact members 320, 330 to ensure a connection between the first and second contact members 320, 330 and the flexible cable 340.

The outer case 370 may be secured about the tray member 310 as described above, or in any other suitable manner. Similarly, the seal member 380 may be secured about the first and second contact members 320, 330 and adjacent to the tray member 310 as described above, or in any other suitable manner.

With reference now to FIGS. 16-22, another embodiment of the present disclosure is shown generally as plug assembly 400. The plug assembly 400 is substantially similar to the plug assemblies described herein and will only be described in detail to the extent necessary to fully disclose the aspects of the present disclosure.

Figure 16:
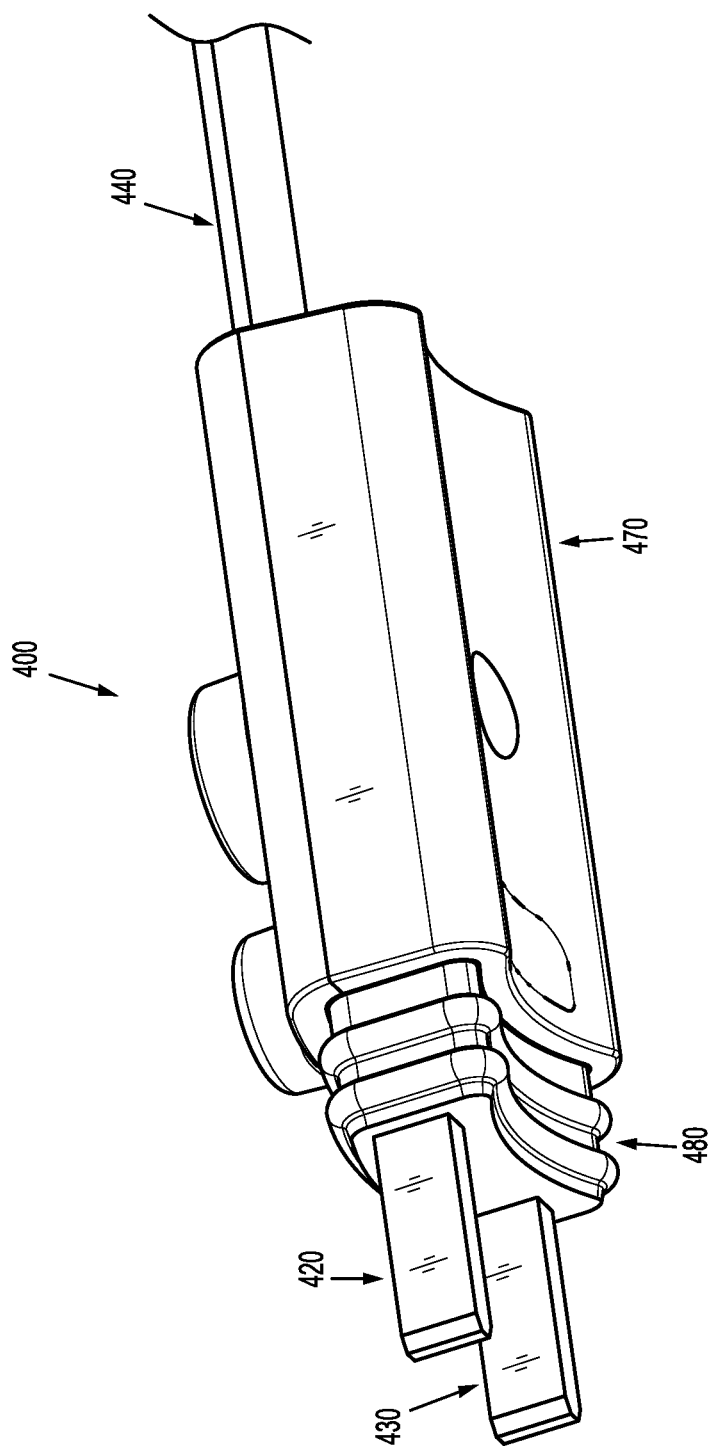
FIG. 16 is a perspective view of a plug assembly according to another embodiment of the present disclosure.

With particular reference to FIG. 16, the plug assembly 400 includes a tray member 410, first and second contact members 420, 430 supported within and extending from the tray member 410, a flexible cable 440 connected to and extending from the first and second contact members 420, 430, an outer case 470 received about the tray member 410, and a seal member 480 received about the first and second contact members 420, 430 adjacent the outer case 470.

Figure 17:
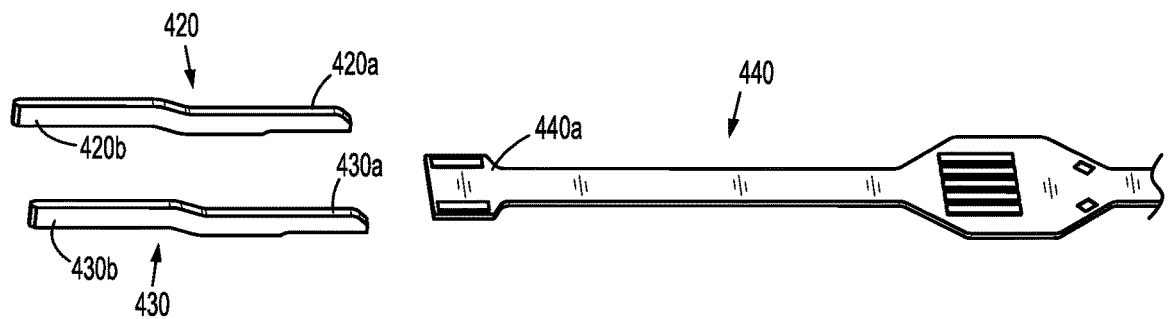
FIG. 17 is a perspective view of contact members and a flexible cable of the plug assembly shown in FIG. 16, with parts separated.
Figure 18:
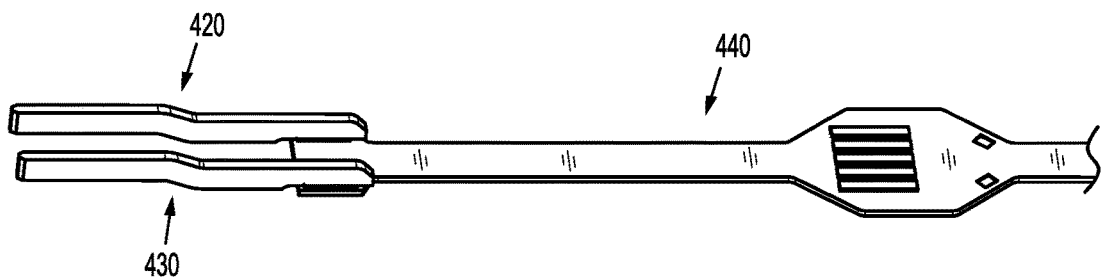
FIG. 18 is a perspective view of the contact members and the flexible cable shown in FIG. 17, connected to one another.
Figure 19:
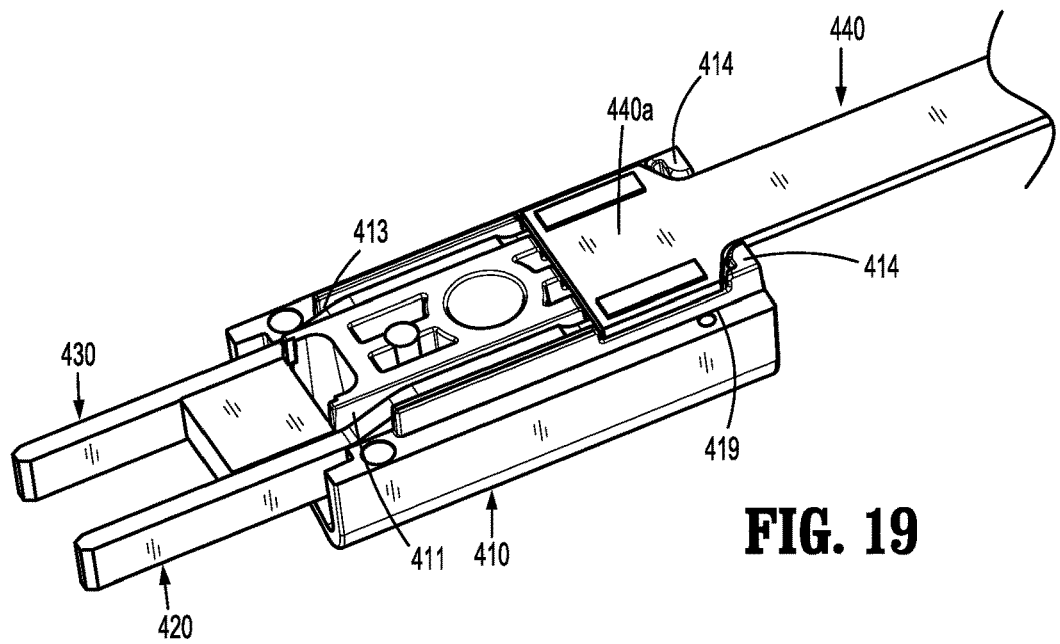
FIG. 19 is a perspective view of the connected contact members and flexible cable shown in FIG. 18 and received within a tray member.
Figure 20:
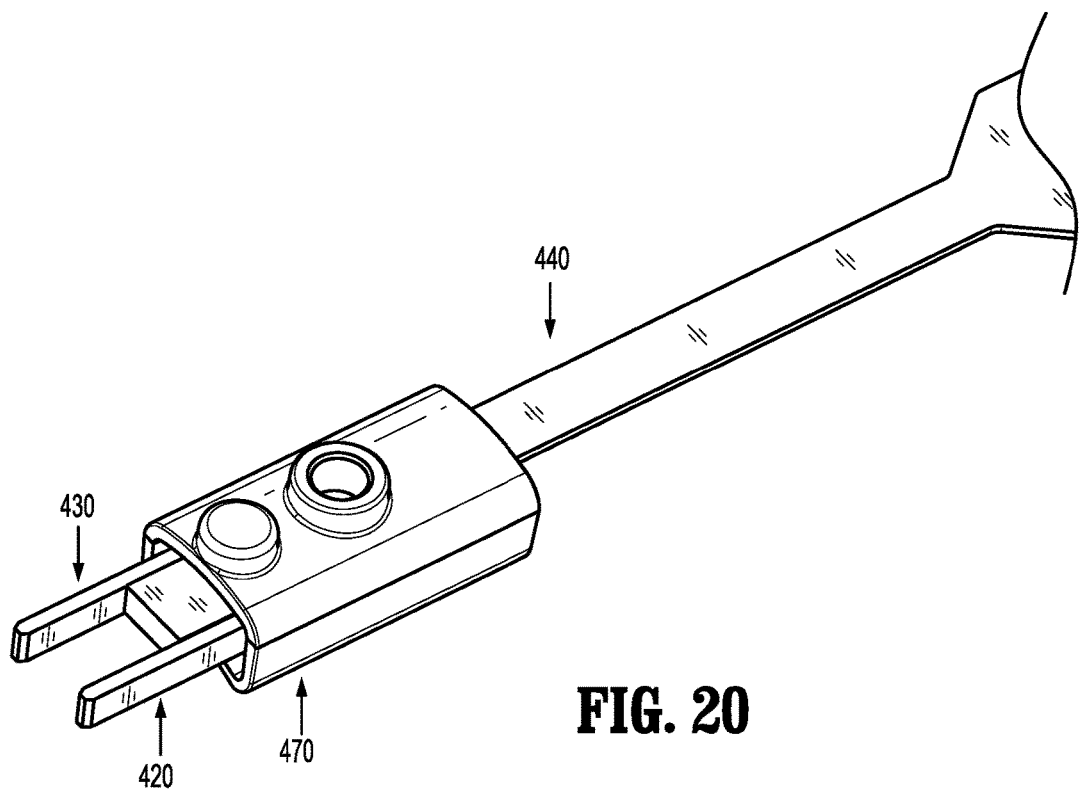
FIG. 20 is a perspective top view of plug assembly shown in FIG. 16, with without a seal member.
Figure 21:
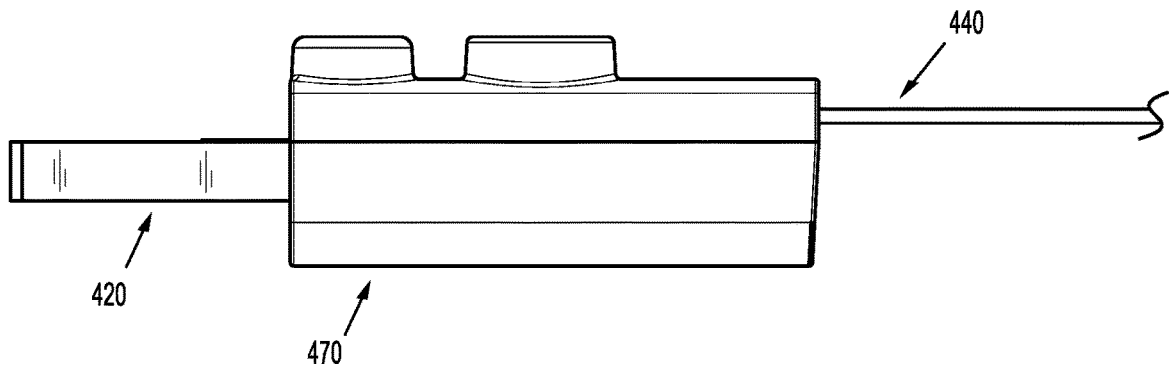
FIG. 21 is a side view of the plug assembly without the seal member shown in FIG. 20.
Figure 22:
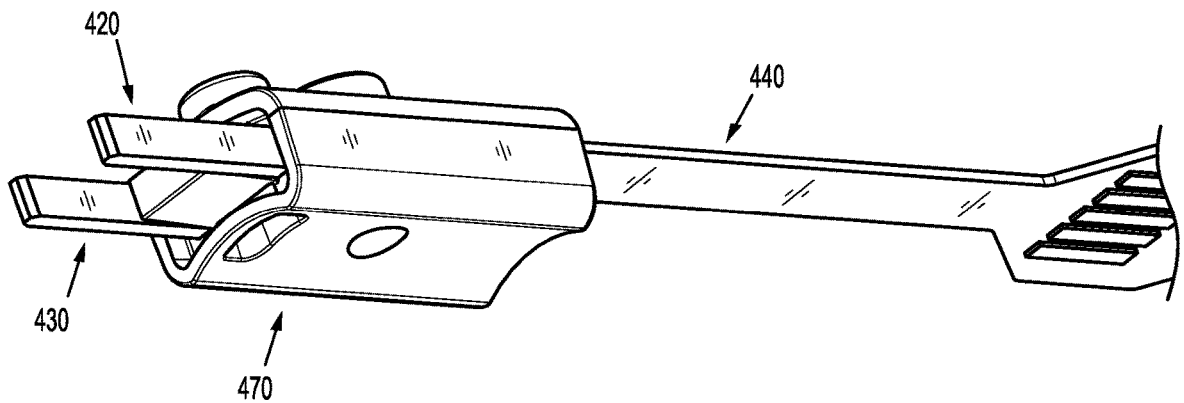
FIG. 22 is a perspective bottom view of the plug assembly without the seal member shown in FIG. 20.

Turing to FIG. 17, each of the first and second contact members 420, 430 includes a proximal portion 422a, 432a, respectively, and a distal portion 422b, 432b, respectively. The flexible cable 440 includes a distal portion 340a having first and second contact portions 442, 444. The first contact portion 442 of the flexible cable 340 is secured to the proximal portion 422a of the first contact member 420 and the second contact portion 444 of the flexible cable 440 is secured to the proximal portion 432a of the second contact member 430 in any suitable manner. In embodiments, and as shown, the first and second contact portions 442, 444 are soldered to the respective first and second contact members 420, 430.

Once the flexible cable 440 is secured to the first and second contact members 430, 440, the first and second contact members 430, 440 are received within respective first and second channels 411, 413 of the tray member 410 and the distal portion 440 of the flexible cable 440 is received within a recess 419 of the tray member 410. A pair of posts 414 engages the distal portion 440 of the flexible cable 440, thereby preventing the flexible cable 440 from being pulled from the tray member 410. An epoxy or other material may then be injected, or otherwise received, within the first and second channels 411, 413 to further secure the first and second contact members 420, 430 and the distal portion 440a of the flexible cable 440 within the tray member 410.

The outer case 470 may be secured about the tray member 410 as described above, or in any other suitable manner. Similarly, the seal member 480 may be secured about the first and second contact members 420, 430 and adjacent to the tray member 310 as described above, or in any other suitable manner.

It will be understood that various modifications may be made to the embodiments disclosed herein. For example, the components of the surgical stapling device can be formed of any material suitable for surgical use and having the required strength characteristics. Therefore, the above description should not be construed as limiting, but merely as exemplifications of preferred embodiments. Those skilled in the art will envision other modifications within the scope and spirit of the claims appended hereto.

The invention claimed is:

1. A surgical stapling device comprising:
   a handle assembly;
   an adapter assembly extending from the handle assembly, the adapter assembly including a distal portion configured for operable engagement with a loading unit; and
   a plug assembly disposed within the distal portion of the adapter assembly and configured for electrical connection with a chip assembly in a loading unit, the plug assembly including:
      a tray member;
      first and second contact members received within and extending distally from the tray member, each of the first and second contact members including proximal and distal portions and an extension formed on the proximal portions; and
      first and second elongated electrical conductors in electrical connection with the first and second contact members and extending proximally from the tray member, each of the first and second elongated electrical conductors including proximal and distal portions and a loop formed on the distal portion, the loop of each of the first and second elongated electrical conductors being received about the extension of the respective first and second contact member;

an outer case formed about the tray member and the proximal portion of the first and second contact members; and a seal member received about the first and second contact members adjacent the outer tray.

2. The surgical stapling device of claim 1, wherein the outer case of the plug assembly is overmolded about the tray member and the proximal portion of the first and second contact members.

3. The surgical stapling device of claim 1, further including a loading unit, wherein the loading unit includes a chip assembly configured for electrical connection with the plug assembly.

4. The surgical stapling device of claim 1, wherein the plug assembly further includes a block member received between the first and second contact members.

5. The surgical stapling device of claim 1, wherein the tray member defines first and second channels and the first and second contact members are received within the respective first and second channels.

6. The surgical stapling device of claim 5, wherein the first and second elongated electrical conductors are received within the respective first and second channels.

7. The surgical stapling device of claim 6, wherein the first and second contact members and the first and second elongated electrical conductors are secured within the respective first and second channels with a sealant material.

8. The surgical stapling device of claim 7, wherein the sealant material is a thermoset resin.

9. The surgical stapling device of claim 1, wherein the outer case includes a cylindrical projection configured to facilitate connection of the plug assembly with the adapter assembly.

10. The surgical stapling device of claim 1, wherein the first and second elongated electrical conductors are electrically connected to the handle assembly.

11. The surgical stapling device of claim 1, wherein the outer case includes a distally extending extension and the seal member is secured to the extension.

12. A plug assembly configured for electrical connection with a chip assembly in a loading unit, the plug assembly comprising:

a tray member;

first and second contact members received within and extending distally from the tray member, each of the first and second contact members including proximal and distal portions and an extension formed on the proximal portions; and first and second elongated electrical conductors in electrical connection with the first and second contact members and extending proximally from the tray member, each of the first and second elongated electrical conductors including proximal and distal portions and a loop formed on the distal portion, the loop of each of the first and second elongated electrical conductors being received about the extension of the respective first and second contact member;

an outer case formed about the tray member and the proximal portion of the first and second contact members; and a seal member received about the first and second contact members adjacent the outer tray.

13. The plug assembly of claim 12, wherein the outer case is overmolded about the tray member and the proximal portion of the first and second contact members.

14. The plug assembly of claim 12, further including a block member received between the first and second contact members.

15. The plug assembly of claim 12, wherein the tray member defines first and second channels and the first and second contact members are received within the respective first and second channels.

16. The plug assembly of claim 12, wherein the first and second elongated electrical conductors are received within the respective first and second channels.

17. The plug assembly of claim 16, wherein the first and second contact members and the first and second elongated electrical conductors are secured within the respective first and second channels with a sealant material.

18. The plug assembly of claim 17, wherein the sealant material is an epoxy.

19. The plug assembly of claim 12, wherein the outer case includes a cylindrical projection configured to facilitate connection of the plug assembly with an adapter assembly.

20. The plug assembly of claim 12, wherein the outer case includes a distally extending extension and the seal member is secured to the extension.

* * * * *